United States Patent [19]  
Ortiz et al.

[11] Patent Number: 4,988,875
[45] Date of Patent: Jan. 29, 1991

[54] NEAR INFRARED POLYETHYLENE INSPECTION SYSTEM AND METHOD

[75] Inventors: Marcos G. Ortiz, Freehold; Marsha S. Stix, Tinton Falls, both of N.J.

[73] Assignee: AT&T Bell Laboratories, Murray Hill, N.J.

[21] Appl. No.: 283,650

[22] Filed: Dec. 13, 1988

[51] Int. Cl.[5] .................... G01N 21/00; G01N 21/01; G01N 21/88; G01N 21/89
[52] U.S. Cl. .................................. 250/330; 250/562; 250/563; 250/358.1; 250/359.1; 250/341
[58] Field of Search ............ 250/562, 563, 564, 359.1, 250/341, 358.1, 330, 339; 356/73.1

[56] References Cited

U.S. PATENT DOCUMENTS

| | | | |
|---|---|---|---|
| 3,870,884 | 3/1975 | Williams | 250/339 |
| 4,208,126 | 6/1980 | Cheo et al. | 250/341 |
| 4,302,108 | 11/1981 | Timson | 250/359.1 |
| 4,363,966 | 12/1982 | Cheo | 250/341 |
| 4,692,799 | 10/1987 | Saitoh et al. | 250/562 |
| 4,710,627 | 12/1987 | Baltes et al. | 250/239 |
| 4,764,681 | 8/1988 | Michalski et al. | 250/563 |

OTHER PUBLICATIONS

Jenkins et al., "*Fundamentals of Optics*", McGraw-Hill Book Company, Inc., N.Y., pp. 201-205.

B. W. Lerch et al., "Armorless Cable Manufacture", Bell System Tech. Jnl., Jul. 1964, pp. 1222-1229.
J. H. Ausubel et al., Ed., "Lasers Invention to Application", National Academy of Engineering, 1987, pp. 40-44.

Primary Examiner—Constantine Hannaher
Assistant Examiner—Edward J. Glick
Attorney, Agent, or Firm—Richard B. Havill; Oleg E. Alber

[57] ABSTRACT

A sample inspection arrangement incorporates a sample of polyethylene with an included defect, or flaw, a light source containing near infrared wavelengths, and a video camera. Polyethylene has relatively high spectral transmissivity for wavelengths in the band of near infrared wavelengths. The video camera collects data from a beam of the near infrared light which either reflects from or is transmitted directly through a portion of the polyethylene sample. Data is collected from both defect free portions of the polyethylene sample and portions of polyethylene sample including at least one defect. A visual image of the polyethylene sample and included defect is produced on either a video monitor, a paper print out, or a photograph. The method for inspecting a sample of cable or a continuously moving section of cable also is described.

10 Claims, 6 Drawing Sheets

NEAR INFRARED POLYETHYLENE INSPECTION SYSTEM AND METHOD

This invention relates to an inspection system and the method of operating that system for inspecting polyethylene jacketed cable.

BACKGROUND OF THE INVENTION

In the field of insulated cable manufacture, electrical cables containing metallic conductors and communications cables containing optical fibers and metallic conductors typically are enclosed in a polyethylene jacket. Many of those cables either carry very high voltage electrical energy or are deployed in a moist environment. Both the high voltage and the moist environment raise great concern over the possibility of a defect, or flaw in the cable jacket causing a serious failure of the cable facility once it is put into service. Such a failure is expensive to repair both because of the actual cost of making a physical repair and because of lost revenue resulting from an interruption of services.

As step toward preventing unscheduled failures of installed cables providing needed services, the manufactures of electrical and optical fiber cables have been developing apparatus and methods for inspecting polyethylene cable jackets for defects, or flaws.

One such inspection system has been disclosed by B. W. Lerch et al., in the Bell System Technical Journal, Volume XLIII, Number 4, Part 1, on pages 1225-1229. That system measures the capacitance of the polyethylene jacket. The capacitance has a constant value for all of the inspected polyethylene jacket which is defect free, or flawless. Variations of the capacitance are found anywhere along the cable where a defect is included in the polyethylene jacket or where there is an absence of polyethylene.

Another inspection system is disclosed by the Electric Power Research Institute in the following series of reports: (1) "A Far-Infrared Laser Scanner for High-Voltage Cable Inspection," Oct. 1982, (2) "Far-Infrared Inspection of Cable Insulation," Apr. 1978, and (3) "Laser Detection of Voids and Contaminants in Polyethylene-Insulated Power Cable," Dec. 1979. In this system, far-infrared light is directed at the polyethylene jacketed cable. At least some of the far-infrared light, reflected from the surface of the polyethylene or from the surface of a defect within the polyethylene, is detected by an optical device. A summary description of the inspection system, described in this series of reports, is present by J. H. Ausubel et al., Ed. in "Lasers Invention to Application", National Academy Press, 1987, pages 40–44.

Both of the aforementioned arrangements have problems detecting and displaying accurate, unambiguous data relating to existing defects within a polyethylene cable jacket. The inspection system apparatus and the inspection operation cost so much or are so inaccurate that there is resistance to using them on widespread basis. Thus much polyethylene jacketed high voltage cable and optical fiber cable is being manufactured with little more than a visual inspection of the polyethylene surface or some other simple inexpensive inspection.

Thus there is a need for an accurate, low cost system for completely inspecting a polyethylene jacketed cable.

The term "polyethylene" as used herein defines a clear polyethylene polymer which is transparent or translucent to an impinging radiation. The polyethylene is typically used as insulation for cables and conductors carrying electrical current, although some other known uses may be contemplated, also. The polyethylene may include additives, such as coloring agents or fillers, which do not affect the transparent or translucent qualities of the polymer to such an extent as to render the polymer opaque to the impinging radiation.

SUMMARY OF THE INVENTION

This problem is solved by a simple inspection arrangement for inspecting polyethylene samples or articles for defects, such as occlusions, voids and the like, and includes a source of light including near infrared radiation and a camera for responding to wavelengths in a range of near infrared light. A source of near infrared light is directed so that a beam of the near infrared light traverses through at least a portion of the sample or is reflected from the sample into the camera for collecting data relating to defect free portions of the cable and to the included defect. More specifically, the prior art problem is solved by an inspection arrangement incorporating the polyethylene jacketed cable to be inspected for flaws or defects, a video camera with magnification lenses which is sensitive to near infrared light in the wavelength range between 800 nm and 1600 nm, and a light source which generates light including the near infrared wavelengths mentioned above. The light source is directed so that it is illuminates the portion of the cable being inspected. The near infrared light is reflected from the cable into the camera for collecting data relating to the polyethylene insulation jacket quality. In an alternate configuration, the infrared light source and the camera are in the same plane and on opposite sides of the portion of cable being inspected. The near infrared light passes through the clear polyethylene and excites the camera on the other side of the cable with data relating to the polyethylene jacket quality.

A non-destructive method for inspecting the bulk of a sample of polyethylene for defects, or flaws, includes the steps of transmitting a near infrared light beam through at least a portion of the sample to a detector in a range of wavelengths of near infrared light; and from the near infrared light beam emerging from the sample, collecting data including relatively uniform values indicating a defect free region of polyethylene in the sample and substantial changes of values indicating at least one defect, or flaw in the polyethylene of the sample.

BRIEF DESCRIPTION OF THE DRAWING

A more complete understanding of the invention may be obtained by reading the following detailed description with reference to the accompanying drawing wherein.

DETAILED DESCRIPTION

Figure 1:
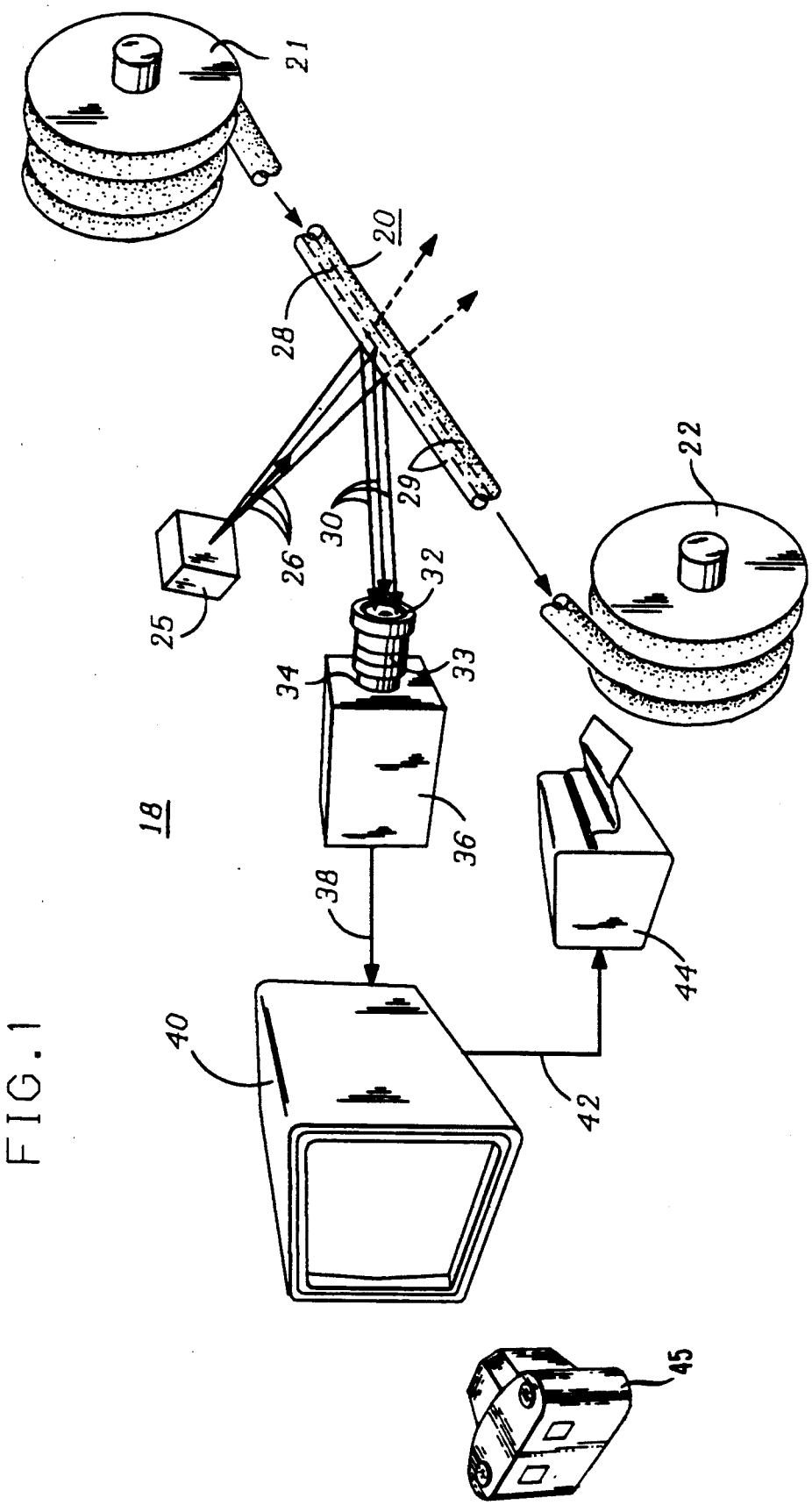
FIG. 1 is diagram of sample inspection arrangement for performing non-destructive reflective optical inspection of the bulk of a polyethylene sample.

Referring now to FIG. 1, there is shown a diagramatic sketch of a near infrared light inspection arrangement 18 for optically inspecting the bulk of a natural polyethylene jacket covering a cable 20. The cable 20 is exposed to the inspection while it is being moved from a storage reel, or cable pan, 21 to a take-up reel, or cable pan, 22. A source of white light 25, such as a halogen quartz lamp, shines an incident beam of light 26 onto a section of the cable. Internally the cable 20 includes an opaque material 28, such as a copper tube, which will reflect any incident light beam. The copper provides a media for transmitting high voltage electrical power. A protective insulating jacket 29, which surrounds the copper, is fabricated from polyethylene.

Reflected light 30, which is reflected both from the surface of the copper and from the surface of the polyethylene jacket 29, is directed to an optical polarizer 32, a magnifying lens system 33, and a long pass filter 34 to a long wavelength video camera 36. Signals received by the video camera 36 are transmitted by way of a conductor 38 to a high resolution video monitor 40 for producing a visible image and another conductor 42 to a paper copy printer 44 for making a printout of the visual image. A photographic copy can be made by a Polaroid Screen Shooter camera 45.

Figure 2:
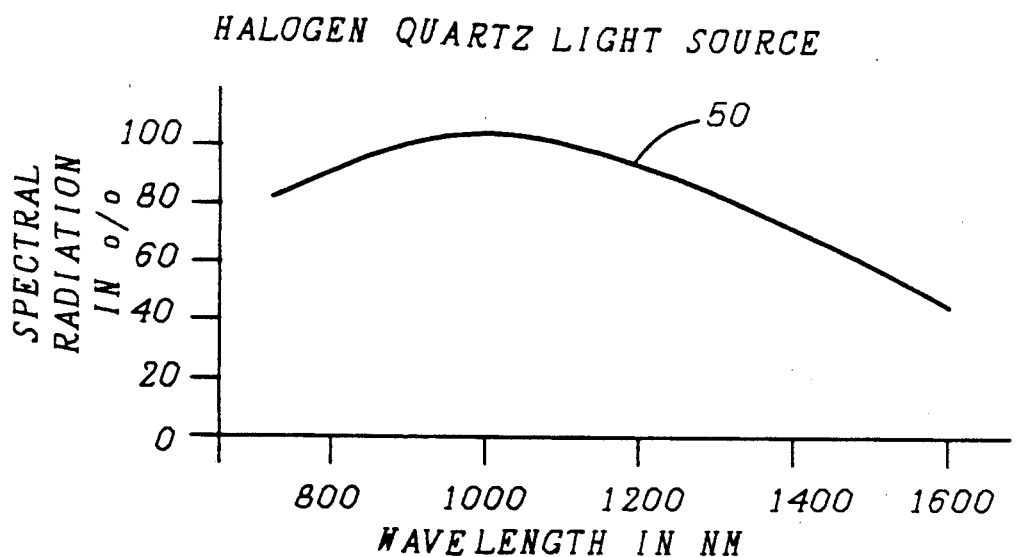
FIG. 2 is a graph of the spectral radiation from a halogen quartz light source.

Curve 50 shown in FIG. 2 represents a graph of the operating characteristic of the halogen quartz lamp, or white light source 25, shown in FIG. 1. The optical, or spectral, radiation of energy from the light source 25 is given as a percentage of its maximum spectral radiation for a band of wavelengths between 800 and 1600 nanometers. The maximum radiation occurs near the wavelength 1000 nanometers. Such a white light source is available commercially and has a much longer life and lower cost than light-emitting diodes and lasers.

Figure 3:
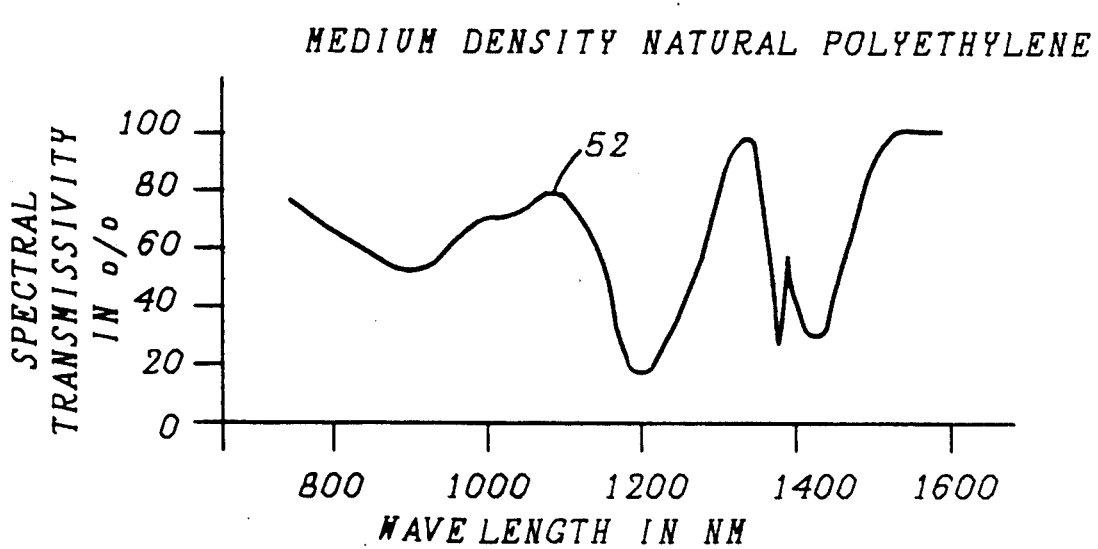
FIG. 3 is a graph of the spectral transmissivity of a medium density polyethylene.

Curve 52 shown in FIG. 3 represents approximate characteristic of the optical or spectral, transmissivity of a sample of a medium density polyethylene, Union Carbide DHDA 1184, which forms the protective insulating cable jacket 29 in FIG. 1. This polyethylene jacket 29 provides mechanical protection for the interior elements of the cable including the copper tube 28 and its contents, which are not shown. Additionally the polyethylene jacket 29 provides insulation for very high voltage which resides in the copper tube 28. The voltage, which may be several thousand volts, is so high that any defects in the polyethylene jacket 29 may cause a breakdown through the insulation and a failure of the cable system. It is noted that transmissivity of the polyethylene, as shown in FIG. 3, is presented as a percentage of the maximum spectral transmissivity over the band of near infrared wavelengths between 800 and 1600 nanometers. Peaks of spectral transmissivity of the natural polyethylene occur near 1100, 1300 1500 nanometers.

Figure 4:
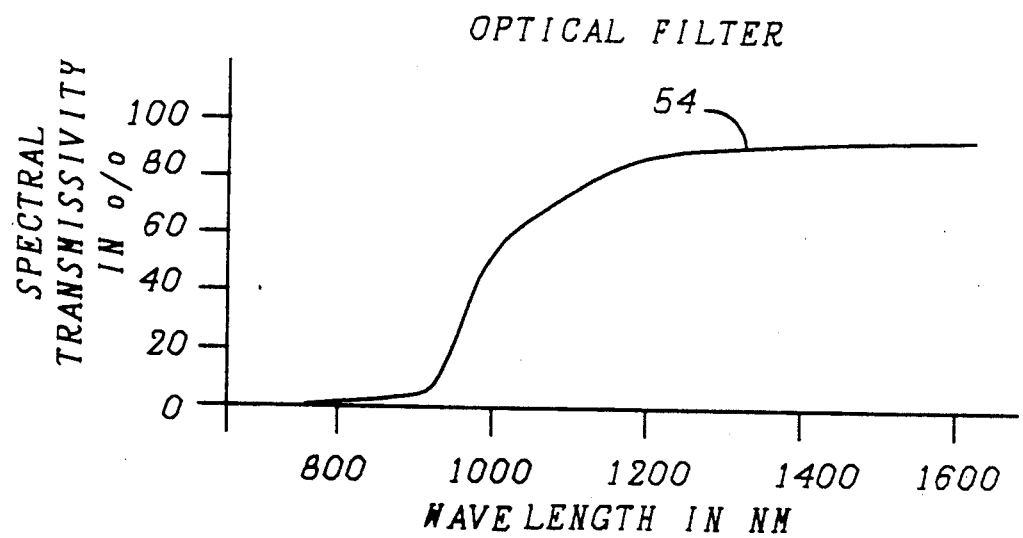
FIG. 4 is a graph of the spectral transmissivity of an optical filter.

Curve 54 shown in FIG. 4 represents an optical or spectral transmissivity characteristic for the long pass filter 34 of FIG. 1. Spectral transmissivity of the filter 34 is shown as a percentage of the maximum spectral transmissivity for the band of near infrared wavelengths between 800 and 1600 nanometers. This filter 34 is selected to filter out visible lightwaves leaving a preponderance of near infra-red wavelengths for inspecting. It is noted that spectral transmissivity rises rapidly starting at 900 nanometers and continues rising to a knee at approximately 1100 nanometers. Thereafter it levels off for longer wavelengths up to 1600 nanometers.

Figure 5:
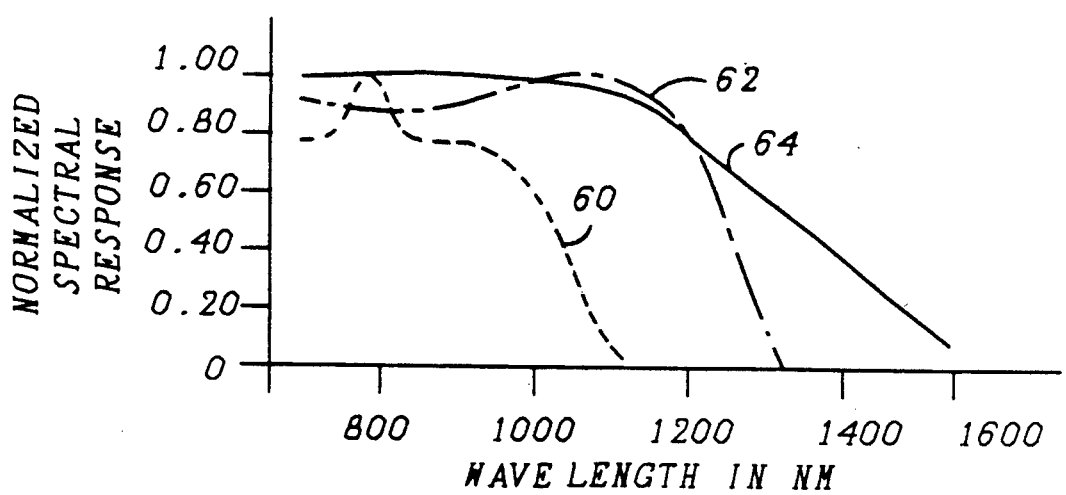
FIG. 5 is a graph of the normalized spectral responses of three types of cameras.

FIG. 5 presents three normalized spectral response characteristic curves 60, 62 and 64 for various commercially available infrared-sensitive electronic video camera equipments. The response curves are normalized for each individual video camera. Characteristic curve 60 shows the spectral response for a fast response CCD video movie camera which is used in an on-line manufacturing process inspection system as well as in an extrusion control system for applying a top quality polyethylene jacket 29 on the cable 20 of FIG. 1. This camera will allow for rapid inspection of a long cable to identify sections which should be inspected more thoroughly. Characteristic curve 62 of FIG. 5 is the curve which represents a slower response video camera which is used in a static inspection station. Such a static inspection will provide a higher resolution image for those sections of cable which need a more thorough inspection. Lastly, curve 64 is the spectral response characteristic curve for a long wavelength video camera which is used for experimental development purposes. This camera provides an even slower response time but the highest resolution image because of special features included in the camera. The curves 60, 62 and 64 are presented as normalized spectral responses over the band of near infrared wavelengths between 800 and 1600 nanometers.

The optical polarizer 32, FIG. 1, and the magnifying lens system 33 are inserted for the following optical effects. The optical polarizer 32 reduces the amount of reflection from the cable surface to the video camera 36 thereby enabling a clearer view of the interior of the polyethylene jacket 29. The magnifying lens system 33 enlarges the image and therefore enables the detection of smaller defects in the polyethylene jacket 29.

What we have discovered is that there are commercially available equipments having efficient optical, or spectral, characteristics in a common band of near infrared wavelengths for optically inspecting the bulk of natural polyethylene. Although the curves of FIGS. 2, 3, 4 and 5 are limited to the range of 800 nm to 1600 nm, other wavelengths up to at least 2400 nm are useful. All of the parts are readily available to be interconnected into the advantageous combination which produces clear images of defects that may reside in the polyethylene or of the absence of (voids in) polyethylene. In particular it is noted that, as shown in FIG. 2, the halogen quartz light source 25 of FIG. 1 produces near maximum spectral radiation for lightwaves having a wavelength of from 900 to 1100 nanometers. The polyethylene jacket 29 and the filter 34 of FIG. 1 transmit the wavelength of 1100 nanometers relatively well as shown in FIGS. 3 and 4. All three video cameras respond well to wavelengths in the band of wavelengths between 1000 and 1100 nanometers. Both of the characteristic curves 62 and 64 for the long wavelength cameras are at very high levels throughout the band of near infrared wavelengths between 800 and 1200 nanometers. In fact the spectral transmissivity characteristic of polyethylene permits the use of other choices of system components having optimum characteristics throughout the range of near infrared wavelengths from 800 to 2400 nanometers.

As a result of the fortuitous wavelength alignment of favorable parts of the various characteristic curves of FIGS. 2 through 5, we have designed a much lower cost inspection system that produces a clear and very accurate video image which can be shown on the screen of the video monitor 40, printed out on a paper copy from the printer 44, or photographed using the Screen Shooter.

Figure 6:
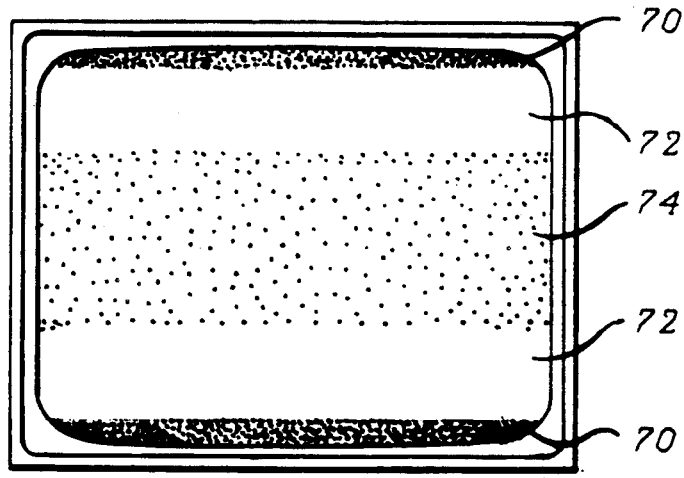
FIG. 6 is a reflective inspection view of a sample of cable covered with defect free polyethylene.

Referring now to FIG. 6, there is shown an example of a clear image of a defect free cable, as produced by the inspection system of FIG. 1. In FIG. 6 there are three areas of interest. A dark dotted area 70 is a view of air surrounding the polyethylene jacket 29 of a cable. Area 70 of the image is dark gray because no light is reflected from the air to the camera. Light gray area 72 results from the polyethylene jacket 29 reflecting some of the incident light. Medium gray area 74 represents the opaque surface of a tube of copper 28 which resides in the center of the cable. Area 74 is a medium gray because some of the light incident on the copper is reflected. It is noted in FIG. 6 that the image is uniform in each of the areas 70, 72 and 74. On the monitor screen, those areas appear as different, but uniform shades of gray, as just described.

Figure 7:
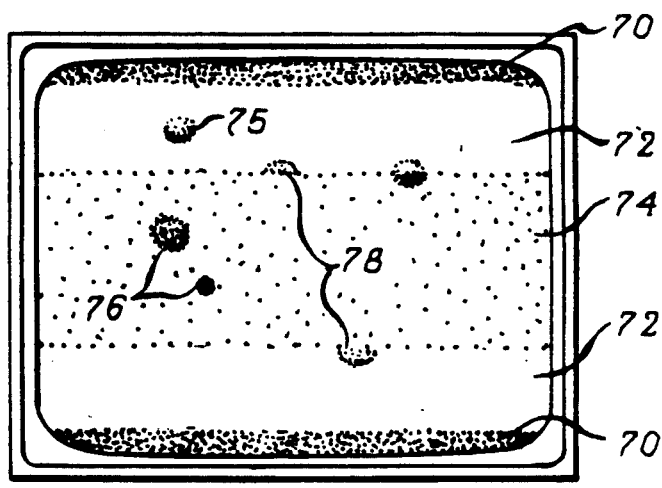
FIG. 7 is a reflective inspection view of a sample of cable covered with polyethylene including flaws, or defects.

FIG. 7 presents an image similar to the image of FIG. 6 except that it shows further information relating to defects. Since the light source 25 of FIG. 1 is shining on one side of the cable 20, some light is reflected from the surfaces that it impinges upon. As described earlier, some wavelengths of the light source penetrate into and are transmitted through the polyethylene. Such light reflects from the surface of defects within the polyethylene. In FIG. 7 there are images of reflections from voids, or bubbles, 75 that are trapped in the middle of the area 72 of polyethylene jacket 29. Additional images of reflections are shown for other bubbles 76 trapped in the polyethylene between the surface of the copper tube 28 (area 74) and the camera 36 of FIG. 1. Also shown in FIG. 7, are images of reflections from bubbles 78 trapped in the polyethylene jacket 29 (area 72) partially hidden behind the copper tube 28 from the camera 36 of FIG. 1. Although not shown in FIG. 7, other defects, such as inclusions, contaminants, pits, lumps of polyethylene, and pieces of charred polyethylene also will show in the image produced by the camera 36 of FIG. 1. Lumps and pits are distinguishable by the geometry in the image. The other listed defects appear as dark spots. Resolution of the images of the reflection is so good that even minor defects are readily detected by visually monitoring either the screen of the video monitor 40, the paper printout from the printer 44, or a photograph from the inspection system of FIG. 1.

The inspection system, as described heretofore, can be used for statically inspecting a sample of cable or for continuously inspecting the natural polyethylene jacket of the cable as the cable passes an inspection station located along a cable fabrication line or wherever the cable is moved from one cable reel or pan to another.

Figure 8:
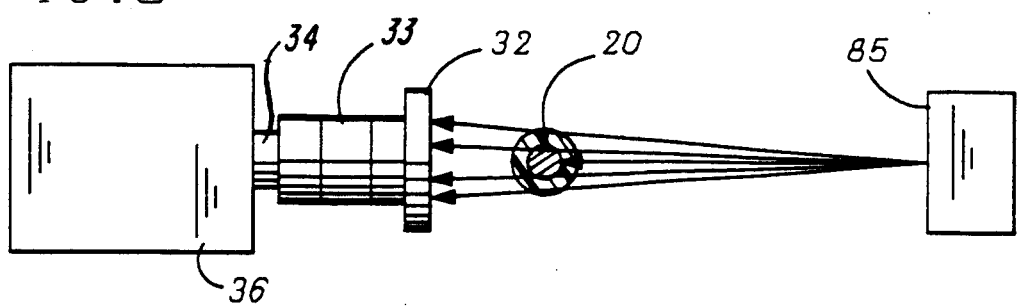
FIG. 8 is a diagram of a sample inspection arrangement for performing non-destructive direct optical inspection via transmission through the bulk of polyethylene jacket.

FIG. 8 shows another inspection system, arranged in accordance with the invention. The cable 20, the optical polarizer 32, the magnifying lens system 33, the long pass filter 34, and the video camera 36 are positioned in alignment with the halogen quartz white light source 85 so that light directed onto cable 20 passes through the cable jacket to the optical polarizer 32, the magnifying lens system 33, the long pass filter 34, and video camera 36. Because the light impinging on the video camera 36 is direct from the light source 85, that light is much brighter than the light which reaches the video camera 36 in the arrangement of FIG. 1. For the arrangement of FIG. 8, special filtering or adjustments to the camera iris may be necessary.

Figure 9:
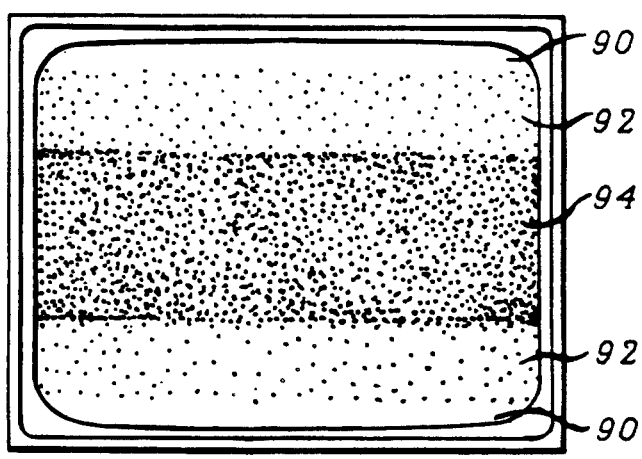
FIG. 9 is a direct inspection view of a sample of cable covered with defect free polyethylene.
Figure 10:
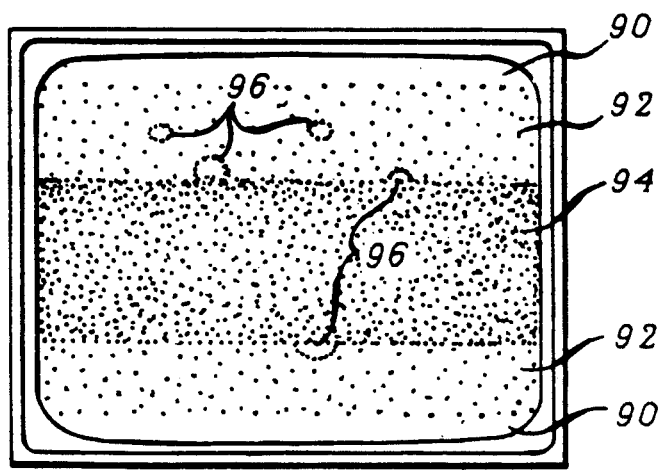
FIG. 10 is a direct inspection view of a sample of cable covered with polyethylene including defects.

As shown in FIGS. 9 and 10, the images produced by the video camera 36 of FIG. 8 are somewhat different than the images produced by the inspection system of FIG. 1.

FIG. 9 shows the image of a defect free section of cable which results from the direct light source arrangement of FIG. 8. In FIG. 9 the areas of air 90 are much brighter because light is transmitted from the light source 85 directly through the air to the camera. Areas 92 of polyethylene jacket 29 are a uniform light gray for a defect free area. The light is transmitted from the light source 85 directly through polyethylene to the video camera. The area 94 of the copper tube is a dark gray shadow because the light from the source 85 is blocked by the opaque copper material.

In FIG. 10 is shown a direct light view of a segment of cable with defects. The cable is surrounded by air which is represented by areas 90. Since the copper tube 28 is opaque, no defects on either side of area 94 are visible to the camera. The shadow of the copper tube obliterates the view of any such defects. Other defects 96 are so located in areas 92 of the polyethylene jacket that they are readily detected. In such locations the appropriate wavelength light shines through the jacket to the defects and the camera. Those defects are visible in the image of FIG. 10, as produced by the camera 36 of FIG. 8.

Figure 11:
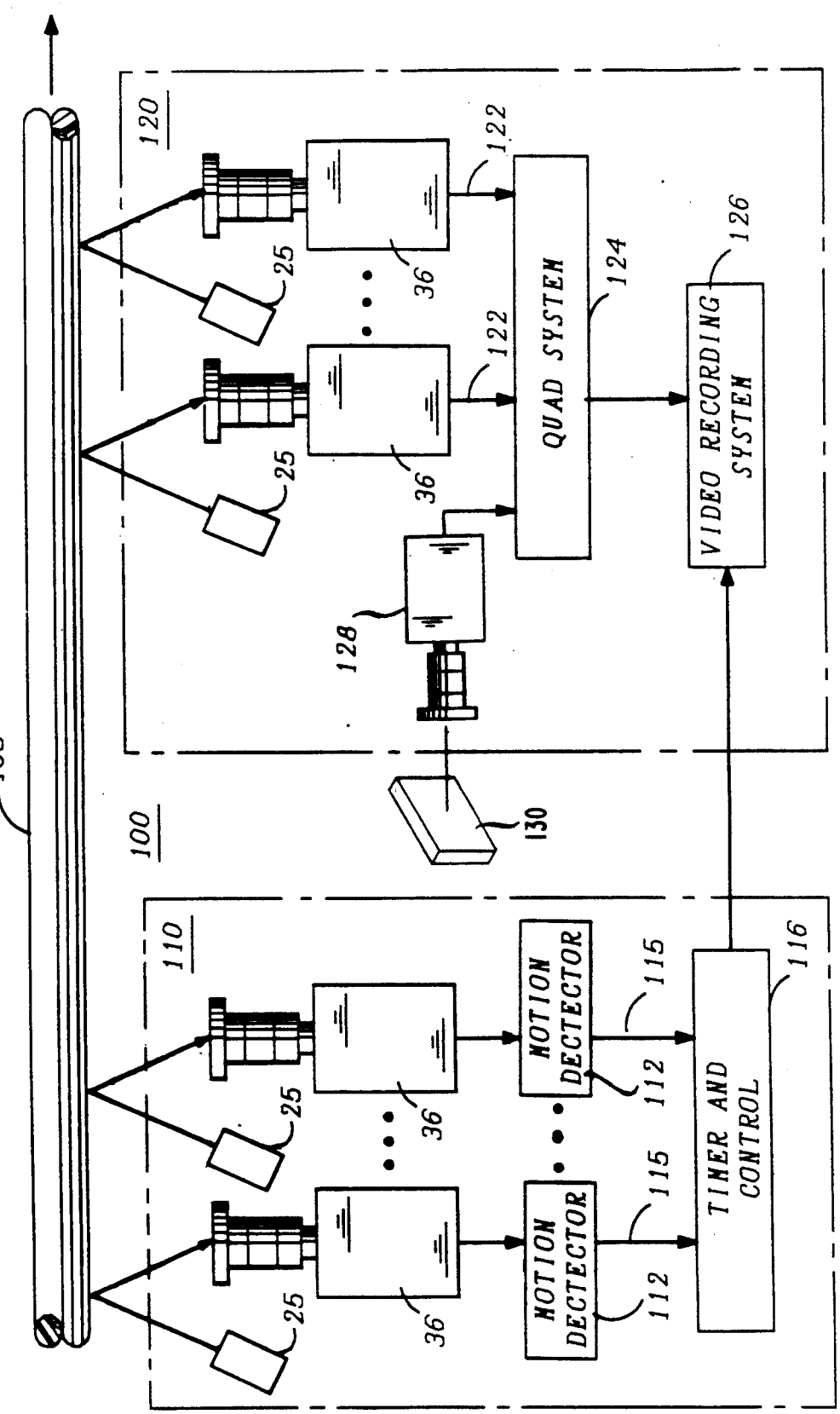
FIG. 11 is a diagram of an arrangement for performing continuous non-destructive reflective inspection of the bulk of a polyethylene jacket of a continuously moving cable.

FIG. 11 shows a near infrared light inspection system 100 for dynamically inspecting a moving cable 105 covered by a polyethylene jacket. Parts of the system 100, which are similar to parts of the test arrangement 18 of FIG. 1, are given the same numerical designation. As the cable 105 of FIG. 11 moves from left to right, it passes an optical detection station 110 having one or more light sources 25 and cameras 36. More than one light source and camera are useful for viewing all of the bulk of the natural polyethylene as it passes the detection station 110. Three light sources and cameras, positioned to view the cable from angles of 120 degrees from each other, can provide view of the entire bulk of the cable jacket.

Each video camera 36 is associated with a motion detector circuit 112. The motion detector circuits determine whether or not there are any defects in the cable jacket as the cable passes the inspection station 110. Each defect that shows in a screened image will cause a variation in the signals delivered from the relevant camera 36 to the associated motion detector circuit 112.

Figure 12:
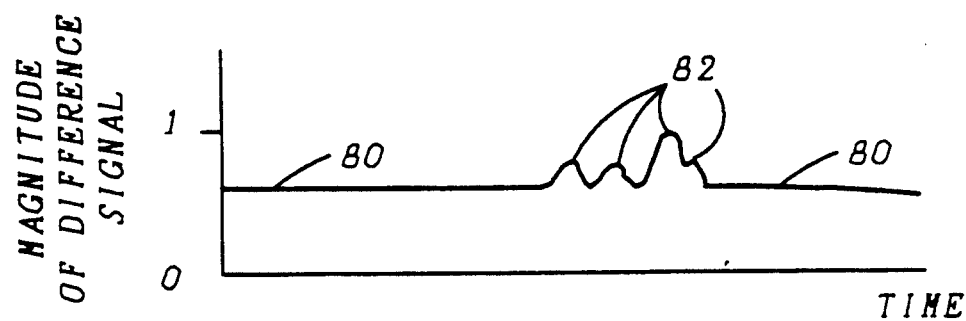
FIG. 12 is a graph showing a response of the arrangement of FIG. 11 to a section of polyethylene containing some defects.

FIG. 12 shows an analog representation of the magnitude of a video signal produced by one of the video cameras 36 of FIG. 11. While the video cameras are scanning any of the uniform gray parts of the cable having a defect free jacket of polyethylene and copper tube, the video signal, represented by the straight portion 80, has a uniform magnitude. Whenever a defect occurs in the natural polyethylene, the magnitude of the video signal changes, as shown by the various peaks 82. The motion detector circuits 112 detect these variations in the video signals. Leads 115 carry signals, produced by the motion detector circuits 112, to a timer and control circuit 116 whenever the polyethylene jacket contains a defect and fails inspection.

The timer and control circuit 116 responds to the signals on the leads 115 and produces a time delayed signal representing the occurrence of any defect in the polyethylene jacket. The time of delay is determined by the speed of the cable and the distance between the detection station 110 and a recording inspection station 120. The time delayed signal from the time and control circuit 116 is timed to occur when the defective segment of cable is positioned for inspection by the recording inspection station 120.

The optical arrangement of the light sources and cameras of the recording inspection station is similar to the detection station 110. In the recording inspection station 120, instead of detecting the defects, the video signals reprsenting the images of the defective segment of polyethylene jacket are transmitted by way of cables 122 through a quad combining system 124 to a video recording system 126. The quad combining system 124 combines signals from up to four video camera sources into four video signal windows at its output. That output is delivered to either the video recording system 126, to a video monitor (not shown) or to both. The video data representing the image of the defective segment of cable is recorded electronically together with the output of a visual spectrum video camera 128. The video camera 128 collects various information from a display panel 130. That information includes speed of the cable, location of the cable area being documented, cable identification number, etc. From the video recording, an image is produced either on a video monitor, a paper print out, or a photograph.

The near infrared light inspection system 100 for dynamically inspecting a moving cable has some advantages over known inspection arrangements. The system 100 provides much clearer and more accurate inspection data than is provided by the prior art capacitance measuring system. It also provides at least as clear and accurate inspection data as that provided by the prior art far infrared inspection system. Importantly, the system 100 is much less expensive than the far infrared inspection system. Operationally, the system 100 produces images, associated with specific locations along the cable. Those images can be evaluated either visually or, by image processing for the purpose of eliminating some cable locations for close inspection.

The foregoing describes an illustrative near infrared inspection system for detecting defects in natural polyethylene used as a cable jacket. Features of the illustrative system and its method of operation and of other inspection systems and their methods of operation made obvious in view thereof are considered to be covered by the appended claims.

We claim:

1. An inspection system for inspecting articles comprising polyethylene for possible defects, including voids, which comprises a source of a beam of electro-optical radiation within a near infrared wavelength range between 800 nm and 2400 nm, a camera responsive to the electro-optical radiation with wavelengths in said wavelength range for collecting data relating to the article and possible included defects, the camera being capable of operating on said certain wavelengths at which said plastic material has a high spectral transmissivity characteristic, said source and said camera are positioned each relative to another and to the article so that the camera receives at least a portion of the light beam radiation, directed from the source onto the said article, as a radiation reflected from at least the defects in the article.

2. An inspection system in accordance with claim 1, further comprising means connected with the camera for converting the collected data into a visual image showing the polyethylene and any included defect.

3. An inspection system, in accordance with claim 1, wherein the camera is an electronic movie camera provided with a polarizer and a long pass filter.

4. An inspection system, in accordance with claim 1 wherein said common wavelength range is between approximately 800 and 1600 nanometers.

5. An inspection system, in accordance with claim 1, further comprising means for moving the sample with respect to the camera; and means connected with the camera for detecting differences in the collected data, as the sample is moved with respect to the camera.

6. An inspection system of claim 1 in which said article is an elongated conductor encapsulated in said plastic material.

7. A test method comprising the steps of reflecting a near infrared light beam within a wavelength range of from 800 to 2400 nm from a polyethylene sample to a video camera responsive to light waves in said wavelength range;

collecting, from the reflected near infrared light beam, data including relatively uniform values indicating a flawless region of the polyethylene sample and substantial changes of values indicating a flaw in the polyethylene sample, and converting the collected data into a visual image showing the polyethylene sample and the flaw, if any.

8. A test method, in accordance with claim 7, comprising the further steps of moving the sample with respect to the video camera and the near infrared light beam so that different portions of the sample are exposed sequentially to the near infrared light beam; and detecting any changes in the collected data for determining the location of the flaw.

9. A test method, in accordance with claim 7, comprising the further steps of moving the video camera and the near infrared light beam with respect to the sample so that different portions of the sample are exposed sequentially to the near infrared light beam; and detecting any changes in the collected data for determining the location of the flaw.

10. An inspection arrangement comprising: a camera responding to light of wavelengths in the near infrared range between 800 nm and 1600 nm; and a means for producing a near infrared light beam which is directed at a portion of a polyethylene jacketed cable to be inspected, and whose reflection from the cable is captured by the camera and used as data relating to the prsence or absence of defects.

* * * * *